United States Patent [19]

Shibata et al.

[11] Patent Number: 5,750,515
[45] Date of Patent: May 12, 1998

[54] CANCER METASTASIS INHIBITOR

[75] Inventors: Jiro Shibata, Iruma; Konstanty Wierzba, Sayama; Koji Murakami; Yuji Yamada, both of Tokorozawa; Koichi Shudo, Tokyo, all of Japan

[73] Assignee: Taiho Pharmaceutical Co., Ltd., Tokyo, Japan

[21] Appl. No.: 737,799

[22] PCT Filed: Apr. 10, 1996

[86] PCT No.: PCT/JP96/00980

§ 371 Date: Nov. 26, 1996

§ 102(e) Date: Nov. 26, 1996

[87] PCT Pub. No.: WO96/32101

PCT Pub. Date: Oct. 17, 1996

[30] Foreign Application Priority Data

Apr. 10, 1995 [JP] Japan .................. 7-083803

[51] Int. Cl.⁶ .............. A61K 31/695; A61K 31/20; A61K 31/19

[52] U.S. Cl. ............ 514/63; 514/569; 514/559; 514/568

[58] Field of Search ............ 514/63, 559, 568, 514/569

[56] References Cited

U.S. PATENT DOCUMENTS 5,081,271  1/1992  Shudo .................. 556/106
5,155,249  10/1992  Shudo .................. 556/419

FOREIGN PATENT DOCUMENTS 1-249783  10/1989  Japan .
2-247185  10/1990  Japan .
7-330595  12/1995  Japan .

Primary Examiner—Jerome D. Goldberg
Attorney, Agent, or Firm—Nikaidko, Marmelstein, Murray & Oram LLP

[57] ABSTRACT

The present invention relates to a cancer metastasis inhibitor comprising a benzoic acid derivative as an active ingredient represented by the formula (I)

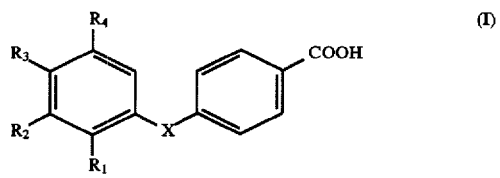

wherein $R_1$, $R_2$, $R_3$ and $R_4$ are the same or different and each represents hydrogen atom, hydroxyl group or trimethylsilyl group, or $R_3$ and $R_4$ are bonded to each other to form a tetramethylene group substituted with lower alkyl group, and X represents group —COCH=C(OH)—, group —NHCO— or group —CONH—, provided that when $R_3$ and $R_4$ are bonded to each other to form a tetramethylene group substituted with lower alkyl group, X is group —COCH=C(OH)— or group —CONH—, use of the benzoic acid derivative for preparing the cancer metastasis inhibitor and method of inhibiting cancer metastasis, characterized in that an effective amount of the benzoic acid derivative is administered to a mammalian animal for inhibiting metastasis of cancer. The benzoic acid derivative represented by the above formula (I) has extremely good metastasis inhibiting properties.

4 Claims, No Drawings

CANCER METASTASIS INHIBITOR

TECHNICAL FIELD

The present invention relates to a cancer metastasis inhibitor that markedly inhibits the metastasis of cancer cells.

BACKGROUND ART

Recently, the cancer treatment has notably progressed. Especially, the success rate of cure of a primary cancer by surgery or radiotherapy has been improved, thereby contributing greatly to the progress of the cancer treatment. However, even if the primary cancer is completely removed, the patient will often die eventually because of the cancer relapse caused by cancer metastasis. Accordingly, there were limitations to the complete blocking of cancer metastasis using surgery, radiotherapy or the like, and therefore the metastasis of a cancer to distant tissue is still a direct or indirect cause of patients' death.

Currently, the mechanism of cancer metastasis is presumed as follows. That is, (1) cancer cells proliferate in a primary cancer colony; (2) blood vessels are newly formed; (3) the malignant cancer cells infiltrate and penetrate the newly formed blood vessels; (4) the cancer cells circulate within the human body; (5) the cancer cells reach a target organ; (6) the cancer cells extravasate from blood vessels; (7) the cancer cells proliferate in the target organ; and (8) a metastatic focus is formed.

To date, many chemotherapeutic agents (antineoplastic agents) have been known. These agents are used as pharmaceuticals that serve to act on the above process (1) of the above mechanism, since they reduce the size of tumors and exhibit direct anti-proliferation and cytocidal properties against cancer cells. However, these agents are never satisfactory in that they cause various kinds of adverse reaction, such as toxicity to bone marrow, and almost can not act on the other stages of metastatic processes.

Generally, cancer metastasis inhibitors are intended not only to prevent the metastasis of cancer cells but also to prevent the growth of a micro metastatic focus formed so as to interdict the metastasis and relapse of a cancer. So, the evaluation for the cancer metastasis inhibitors is totally different from that for the typical antineoplastic agents, which, in turn, are expected to diminish tumor size by their cytocidal properties. Accordingly, in view of the metastatic process, a new type of pharmaceutical, which causes little adverse reaction and can be administered for a long period of time, is extremely valuable and has been expected.

As apparent from the foregoing, it has gradually been recognized that from the view point of cancer treatment, blocking of cancer metastasis is an important matter to be achieved in treating a cancer, and in the United States of America, United Kingdom, etc., clinical studies of cancer metastasis inhibitors have been conducted. Recently, several genes considered to be related to cancer metastasis and infiltration have been discovered from one to another, and it has been reported that retinoid compounds, in particular all-trans-retinoic acid can prevent the expression of these genes to interdict metastasis and infiltration of cancer cells in concentration dependent manner. However, their effects have proved not so satisfactory. Therefore, no effective cancer metastasis inhibitor has been developed heretofore.

DISCLOSURE OF THE INVENTION

In view of the above-described situation, the present inventors have studied the pharmacological action of some specific benzoic acid derivatives in various respects, which derivatives have not been reported to have cancer metastasis inhibiting properties. As a result, they have found that these compounds have extremely effective properties for inhibiting metastasis of cancer to thereby complete the present invention.

More specifically, the present invention provides a cancer metastasis inhibitor comprising, as an active ingredient, a benzoic acid derivative represented by the following formula (I)

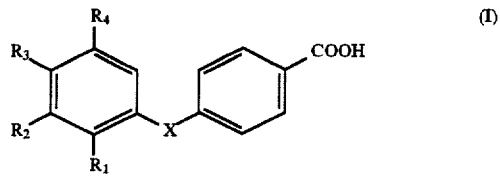

wherein $R_1$, $R_2$, $R_3$ and $R_4$ are the same or different and each represents hydrogen atom, hydroxyl group or trimethylsilyl group, or $R_3$ and $R_4$ are bonded to each other to form a tetramethylene group substituted with lower alkyl group, and X represents group —COCH=C(OH)—, group —NHCO— or group —CONH—, provided that when $R_3$ and $R_4$ are bonded to each other to form a tetramethylene group substituted with lower alkyl group, X is group —COCH=C(OH)— or group —CONH—.

Further, the present invention provides use of the benzoic acid derivative represented by the above formula (I) for preparing a cancer metastasis inhibitor.

Furthermore, the present invention provides a method for inhibiting metastasis of cancer, characterized in that an effective amount of the benzoic acid derivative represented by the above formula (I) is administered to a mammalian animal for inhibiting metastasis of cancer.

Examples of the lower alkyl group in the benzoic acid derivative represented by the above formula (I) are straight chain or branched chain alkyl groups having 1 to 6 carbon atoms, such as methyl, ethyl, propyl, isopropyl, butyl, tert-butyl, pentyl and hexyl groups, with the preferred examples being straight chain or branched chain alkyl groups having 1 to 4 carbon atoms. Examples of the tetramethylene group substituted with lower alkyl group are the tetramethylene groups having 1 to 8 lower alkyl groups as a substituent, with the preferred example being the tetramethylene group having 2 to 4 lower alkyl groups, and the particularly preferred examples being 1,4-dimethyltetramethylene, 1,1,4-trimethyltetramethylene, 1,4,4-trimethyltetramethylene, 1,1,4,4-tetramethyltetramethylene, etc.

The benzoic acid derivatives represented by the above formula (I) are already known compounds disclosed in Japanese Unexamined Patent Publications Nos. 215581/1987, 249783/1989, 247185/1990 or the like and can be prepared in accordance with the disclosures of the above publications. These compounds are known as pharmaceuticals for cancer treatment or induction of differentiation for cancer cells, but are not known to have cancer metastasis inhibiting properties.

The specific examples of the compound represented by the above formula (I) are 4-[1-hydroxy-3-oxo-3-(5,6,7,8-tetrahydro-5,5,8,8-tetramethyl-3-hydroxy-2-naphthalenyl)-1-propenyl] benzoic acid (hereinafter referred to as "compound Re 80"), 4-[3,5-bis(trimethylsilyl) phenylcarbamoyl] benzoic acid (hereinafter referred to as "compound Am 55S"), 4-[3,5-bis(trimethylsilyl) phenylcarboxamide] benzoic acid (hereinafter referred to as "compound Am 555S")

or the like that are represented by the following structural formulae:

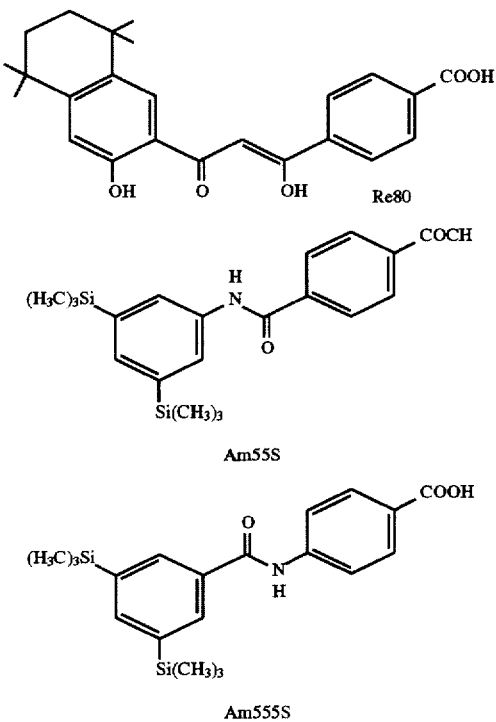

Of the above compounds, the compound Re 80 can be prepared in accordance with the procedure disclosed in Japanese Unexamined Patent Publication No. 215581/1987, the compound Am 55S can be prepared in accordance with the procedure disclosed in Japanese Unexamined Patent Publication No. 249783/1989 and the compound Am 555S can be prepared in accordance with the procedure disclosed in Japanese Unexamined Patent Publication No. 247185/1990.

The cancer metastasis inhibitor of the invention comprises the benzoic acid derivative represented by the above formula (I) as an active ingredient and is formulated in various dosage forms alone or in combination with pharmaceutically acceptable carriers and then administered.

In any cases, these are formulated as pharmaceutical compositions using appropriate pharmaceutically acceptable carriers and in accordance with a conventional formulation method. Examples of the carriers used here are the various diluents or excipients generally used in the usual pharmaceuticals, such as fillers, extenders, binders, disintegrators, surfactants and lubricants.

To inhibit the cancer metastasis of mammalian animals including human beings, the cancer metastasis inhibitor of the invention is administered in not specifically limited dosage forms, but can be administered in a dosage form appropriately selected depending on therapeutic purposes. The typical examples of the dosage forms may include tablets, pills, powders, solutions, suspensions, emulsions, granules, capsules, suppositories, injections, ointments, plasters and the like.

In formulation into the form of tablets, usable examples of carriers include excipients such as lactose, saccharose, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethylcellulose, shellac, methyl cellulose, potassium phosphate and polyvinyl pyrrolidone, disintegrators such as dried starch, sodium alginate, agar powder, laminaran powder, sodium hydrogencarbonate, calcium carbonate, polyoxyethylenesorbitan fatty acid esters, sodium lauryl sulfate, stearic acid monoglyceride, starch and lactose, disintegration suppressors such as saccharose, stearic acid, cacao butter and hydrogenated oil, absorbefacients such as quaternary ammonium bases and sodium lauryl sulfate, humectants such as glycerin and starch, adsorbents such as starch, lactose, kaolin, bentonite and colloidal silicic acid, and lubricants such as purified talc, stearic acid salt, boric acid powder and polyethylene glycol. Further, tablets may be formed into those applied with conventional coatings as needed to give, for example, sugar-coated tablets, gelatin-coated tablets, enteric-coated tablets, film-coated tablets, double coated tablets, multilayer coated tablets, or the like.

Examples of carriers usable in formulation into the form of pills include excipients such as glucose, lactose, starch, cacao butter, hydrogenated vegetable oil, kaolin and talc, binders such as gum arabic powder, tragacanth powder, gelatin and ethanol and disintegrators such as laminaran and agar.

Capsules are formulated by mixing the benzoic acid derivative represented by the above formula (I) with one or more of the above-exemplified various carriers and then filling the resultant mixture in hard gelatin capsules, soft capsules or the like.

As a carrier in formulation into the form of suppositories, it is possible to use, for example, polyethylene glycol, cacao butter, esters of higher alcohol, gelatin and semi-synthetic glyceride or the like.

To formulate injections, it is preferred to sterilize solutions, emulsions or suspensions and to make them isotonic with blood. Usable examples of diluents in formulation into the form of these injections include water, lactic acid solution, ethyl alcohol, propylene glycol, ethoxylated isostearyl alcohol, polyoxylated isostearyl alcohol and polyoxyethylenesorbitan fatty acid esters. In this case, such pharmaceutical preparations may contain sodium chloride, glucose or glycerin in an amount sufficient to prepare isotonic solutions. Further, conventional solubilizing aids, buffers, soothing agents, and the like may also be added.

Examples of diluents usable in formulation into the form of ointments, for example, pastes, creams and gels, include white petrolatum, paraffin, glycerin, cellulose derivatives, polyethylene glycol, silicone and bentonite.

To the above-described preparations, colorants, preservatives, perfumes, flavors, sweeteners and/or the like as well as another pharmaceutical can also be added as needed.

The amount of the benzoic acid derivative of the above formula (I) to be contained in the metastasis inhibitor of the invention is not specifically limited, but may suitably be selected. The preferred amount of the benzoic acid derivative in the pharmaceutical preparation is usually about 1–70 weight %.

No particular limitation is imposed on the administration method for the cancer metastasis inhibitor of the present invention. The administration method is determined depending on the form of the preparation, the age, sex and other conditions of the patient, the severity of a symptom of the patient, and the like. For example, oral administration is used for tablets, pills, powders, solutions, suspensions, emulsions, granules and capsules. The suppository is administered intrarectally. Injections are intravenously administered either by themselves or as mixtures with a usual fluid replacement such as glucose or amino acids, and if necessary, are also administered by themselves intra-arterially, intramuscularly, intracutaneously, subcutaneously or intraperitoneally. Ointments are applied on the skin, the oral mucosa or the like.

The amount of the active ingredient, to be administered, of the cancer metastasis inhibitor of the invention can be suitably chosen depending on the administration method, the age, sex and other conditions of the patient, the severity of the disease and the like. As a general standard, the dose of the benzoic acid derivative represented by the formula (I) may range from about 0.1 to 100 mg/kg/day, preferably from about 0.5 to 50 mg/kg/day. These metastasis inhibitors of the invention can be each administered once a day or in about 2 to 4 portions in a day.

The type of cancer metastasis that can be inhibited by the administration of the cancer metastasis inhibitor according to the present invention is not limited to any particular ones, but include, for example, metastasis to liver, metastasis to lung, metastasis to lymph node and the like.

The benzoic acid derivative represented by the above formula (I) has extremely good metastasis inhibiting properties. So, the compositions comprising the benzoic acid derivative as an active ingredient is useful as a cancer metastasis inhibitor.

BEST MODE FOR CARRYING OUT THE INVENTION

The present invention will hereinafter be described with reference to pharmacological test examples and preparation examples, but shall not be limited thereto.

Pharmacological Test 1 Effect on the experimental liver metastasis

The effect of cancer metastasis inhibition was measured using the compounds Re 80, Am 55S and Am 555S.

<Test Procedure>

KM12L4 (human colon cancer), TMK-1 (human stomach cancer) and A549 (human lung cancer) were each transplanted into the spleen of SPF BALB/c-nu/nu male mice (7 week old) in an amount of $1\times10^6$ cells/mouse. This test was conducted using experimental liver metastasis models.

The test procedure followed the modified Morikawa et al method (*Cancer Research*, 48, 1943–1948, (1988)). That is, the in vitro cultured cells were collected using 0.25% trypsin—0.02% EDTA or 0.02% EDTA and were then washed with physiological phosphate buffer saline. After the number of the cells was counted, the cells were diluted to $10^6$ cells/50 µl. Next, each mouse was incised at their left abdomen after being anesthetized with 30 mg/kg of Nembutal and then the spleen was exposed. With a 28 gauge needle attached syringe, 50 µl of the above-prepared suspension containing $1\times10^6$ cells/50 µl was injected into the spleen. After two minutes, two portions of blood vessels of the spleen were ligated using a Liga clip and the spleen was removed. The incision site was then closed using a kyapher suture. Each of the compounds Re 80, Am 55S and Am 555S, which is an active ingredient of the cancer metastasis inhibitor of the invention, was suspended in 5% ethanol/ olive oil or in 0.5% carboxymethyl cellulose/0.5% Tween 80 (Registered Trademark, produced by Nacalai tesque Co.) and was orally administered to each mouse from next day of the transplantation. In each case, the administration was conducted for three terms, each term consisting of five consecutive administration days and two non-administration days. Evaluation was conducted using the increased life span (ILS) in comparison to the control solvent group as an evaluation index. The ILS of all-trans-retinoic acid (ATRA), known to have cancer metastasis inhibiting properties, was also measured with the same test procedure. The test results are shown in Table 1.

TABLE 1

| Compound No. | Administration Amount (mg/kg) | Increased life span (ILS %) | | |
|---|---|---|---|---|
| | | KM12L4 | TMK-1 | A549 |
| Re 80 | 0.5 | 23 | 36 | 19 |
| | 2 | 34 | 50 | 22 |
| Am 55S | 100 | 14 | 39 | 37 |
| | 300 | 42 | 30 | 6 |
| Am 555S | 4 | 5 | 59 | 57 |
| | 16 | 22 | 71 | 30 |
| ATRA | 8 | — | 22 | — |

As shown in Table 1, the active ingredients of the cancer metastasis inhibitor of the invention, i.e., the respective compounds Re 80, Am 55S and Am 555S remarkably prolonged the survival time of the mouse, and the maximum value of the ILS as compared with the control group was 50% for Re 80, 42% for Am 55S and 71% for Am 555S. Further, as compared with the all-trans-retinoic acid (ATRA), which is known to have cancer metastasis inhibiting properties, the maximum ILS of the respective above-mentioned compounds were higher. Especially, Re 80 and Am 555S exhibited marked advantages. Therefore, it was confirmed that the active ingredients of the cancer metastasis inhibitor of the invention, i.e., the respective compounds Re 80,. Am 55S and Am 555S were effective to inhibit cancer metastasis.

Pharmacological Test Example 2 Tumor Growth Inhibitory Effect

<Test Procedure>

Each of 4-1ST (human stomach cancer) and LC-6 (human lung cancer) cell lines grown subcutaneously as solid tumors in mice, were cut into rectangular pieces measuring 2 mm×2 mm×2 mm and were then transplanted subcutaneously into the right backs of SPF BALB/c-nu/nu male mice (7 week old) by use of a needle for transplantation. Using the equation shown below, the estimated volume of tumor was determined. When the estimated volume of tumor became 100–250 mm$^3$, the mice were allocated. To the grouped mice were administered various doses of Am 555S, 5-fluorouracil (5-FU) and Cisplatin (CDDP). The administration was conducted by the selected method that appeared to be the most effective method for administration of each drug. More specifically, Am 555S was orally administered for three terms, each term consisting of five consecutive administration days and two non-administration days. 5-FU was administered intravenously through the tail vein for consecutive five days, and CDDP was administered once intravenously through the tail vein. After three weeks from the administration commencement, the mice were killed and the tumor growth inhibition rates were determined from the rate of tumor weights to that of the non-treated group, so as to determine the effect of growth inhibition of the tumor. The results are shown in Table 2.

TABLE 2

| Estimated volume of tumor = length × width$^2$/2 (mm$^3$) | | | |
|---|---|---|---|
| Compound No. | Administration Amount (mg/kg) | Tumor Growth Inhibition Rate | |
| | | 4-1ST | LC-6 |
| Am 555S | 8 | 8.7 | 13.7 |
| | 4 | −4.9 | — |
| | 2 | 2.7 | 2.7 |
| 5-FU | 19 | 50.9 | — |
| CDDP | 7 | — | 52.3 |

As shown in Table 2, Am 555S, that is, the active ingredient of the cancer metastasis inhibitor of the invention, exhibited extremely low tumor growth inhibition rates as compared with 5-FU and CDDP that have tumor growth inhibiting properties and are now widely used as antitumor agents. Therefore, Am 555S showed no tumor growth inhibition activity.

Toxicity Test

SPF ICR male mice (5 week old) were used as divided into groups each consisting of 6 mice. To the group to be administered with the compound Re 80, the group to be administered with the compound Am 55S and the group to be administered with the compound Am 555S were orally administered 2 mg/kg of the compound Re 80 per day, 640 mg/kg of the compound Am 55S per day and 16 mg/kg of the compound Am 555S per day for consecutive 3 weeks, respectively. No death occurred in any of the groups. Furthermore, no notable side effect occurred.

PREPARATION EXAMPLE 1

| Tablet | |
|---|---|
| Compound Re 80 | 40 mg |
| Starch | 100 mg |
| Magnesium stearate | 15 mg |
| Lactose | 45 mg |
| Total | 200 mg |

In accordance with the above formula, tablets each weighing 200 mg were prepared in a manner known per se in the art.

PREPARATION EXAMPLE 2

| Granule | |
|---|---|
| Compound Am 55S | 200 mg |
| Lactose | 340 mg |
| Cone starch | 450 mg |
| Hydroxypropylmethyl cellulose | 10 mg |
| Total | 1000 mg |

In accordance with the above formula, granules were prepared in a manner known per se in the art.

PREPARATION EXAMPLE 3

| Capsule | |
|---|---|
| Compound Am 555S | 100 mg |
| Lactose | 170 mg |
| Crystalline cellulose | 77 mg |
| Magnesium stearate | 3 mg |
| Total | 350 mg |

In accordance with the above formula, capsules were prepared in a manner known per se in the art.

PREPARATION EXAMPLE 4

| Injection | |
|---|---|
| Compound Am 555S | 200 mg |
| Distilled water for injection | suitable amount |
| | 5 ml per 1 ampule |

In accordance with the above formula, injections were prepared in a manner known per se in the art.

PREPARATION EXAMPLE 5

| Suppository | |
|---|---|
| Compound Am 555S | 100 mg |
| Witepsol W-35 | 1400 mg |

(Trademark, produced by Dynamite Nobel Co.) 1500 mg per one product

In accordance with the above formula, suppositories were prepared in a manner known per se in the art.

We claim:

1. A method for inhibiting metastasis of cancer of the liver, lung or lymph node, which cancer metastasis is sensitive to treatment with compounds of formula (I), without substantially inhibiting tumor growth, comprising administering to a mammalian animal in need of such inhibition a metastasis inhibiting effective amount of a benzoic acid derivative of formula (I),

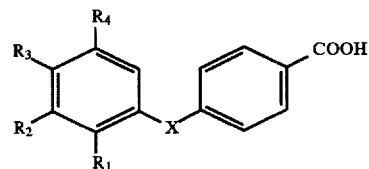

wherein $R_1$, $R_2$, $R_3$ and $R_4$ are the same or different and each represents a hydrogen atom, hydroxyl group or trimethylsilyl group, or $R_3$ and $R_4$ are bonded to each other to form a tetramethylene group substituted with a lower alkyl group, wherein X represents the group —COCH=C(OH)—, the group —NHCO— or the group —CONH—, provided that when $R_3$ and $R_4$ are bonded to each other to form a tetramethylene group substituted with a lower alkyl group, X is the group —COCH=C(OH)—, or the group —CONH—.

2. The method according to claim 1, wherein the benzoic acid derivative represented by the formula (I) is 4-[1-hydroxy-3-oxo-3-(5,6,7,8-tetrahydro-5,5,8,8-tetramethyl-3-hydroxy-2-naphthalenyl)-1-propenyl] benzoic acid.

3. The method according to claim 1, wherein the benzoic acid derivative represented by the formula (I) is 4-[3,5-bis(trimethylsilyl) phenylcarbamoyl] benzoic acid.

4. The method according to claim 1, wherein the benzoic acid derivative represented by the formula (I) is 4-[3,5-bis(trimethylsilyl) phenylcarboxamide] benzoic acid.

* * * * *

UNITED STATES PATENT AND TRADEMARK OFFICE
CERTIFICATE OF CORRECTION

PATENT NO. : 5,750,515

DATED : May 12, 1998

INVENTOR(S) : Shibata et al.

It is certified that error appears in the above-identified patent and that said Letters Patent is hereby corrected as shown below:

Claim 1, line 1, should be amended to read as follows:

1. A method for inhibiting <u>cancer metastasis to</u> the

Signed and Sealed this

Sixteenth Day of March, 1999

Attest:

Q. TODD DICKINSON

*Attesting Officer*   *Acting Commissioner of Patents and Trademarks*